US009427480B2

(12) United States Patent
Santin et al.

(10) Patent No.: US 9,427,480 B2
(45) Date of Patent: Aug. 30, 2016

(54) DUOCARMYCIN ADCS FOR USE IN TREATMENT OF ENDOMETRIAL CANCER

(71) Applicants: Synthon Biopharmaceuticals B.V., Nijmegen (NL); Yale University, New Haven, CT (US)

(72) Inventors: Alessandro Davide Santin, New Haven, CT (US); Peter Johannes Goedings, Nijmegen (NL)

(73) Assignees: Synthon Biopharmaceuticals B.V., Nijmegen (NL); Yale University, New Haven, CT (US)

(*) Notice: Subject to any disclaimer, the term of this patent is extended or adjusted under 35 U.S.C. 154(b) by 0 days.

(21) Appl. No.: 14/859,221

(22) Filed: Sep. 18, 2015

(65) Prior Publication Data

US 2016/0008487 A1    Jan. 14, 2016

Related U.S. Application Data

(63) Continuation of application No. PCT/EP2015/050332, filed on Jan. 9, 2015.

(30) Foreign Application Priority Data

Jan. 10, 2014 (EP) .................................. 14150791

(51) Int. Cl.
| | | |
|---|---|---|
| A61K 47/48 | (2006.01) | |
| A61K 39/395 | (2006.01) | |
| C07D 405/12 | (2006.01) | |
| A61K 45/06 | (2006.01) | |
| C07K 16/40 | (2006.01) | |

(52) U.S. Cl.
CPC ..... *A61K 47/48646* (2013.01); *A61K 39/3955* (2013.01); *A61K 45/06* (2013.01); *A61K 47/48338* (2013.01); *A61K 47/48407* (2013.01); *A61K 47/48484* (2013.01); *A61K 47/48584* (2013.01); *C07K 16/40* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,475,092 A | 12/1995 | Chari et al. | |
| 5,502,068 A | 3/1996 | Lown et al. | |
| 5,579,350 A | 11/1996 | Furukawa et al. | |
| 5,739,350 A | 4/1998 | Kelly et al. | |
| 7,064,117 B2 | 6/2006 | Denny et al. | |
| 7,705,045 B2 | 4/2010 | De Groot et al. | |
| 7,718,688 B2 | 5/2010 | Denny et al. | |
| 8,012,978 B2 | 9/2011 | Zhao et al. | |
| 8,680,293 B2 | 3/2014 | Beusker et al. | |
| 8,889,868 B2 | 11/2014 | Beusker et al. | |
| 2003/0073731 A1 | 4/2003 | Lee | |
| 2004/0033962 A1 | 2/2004 | Tietze et al. | |
| 2005/0014700 A1 | 1/2005 | Boger | |
| 2006/0116422 A1 | 6/2006 | De Groot et al. | |
| 2006/0233794 A1 | 10/2006 | Law et al. | |
| 2009/0010945 A1* | 1/2009 | Alley ............... | A61K 47/48384 514/1.1 |
| 2009/0111805 A1 | 4/2009 | Morris et al. | |
| 2009/0162372 A1 | 6/2009 | King et al. | |
| 2012/0214864 A1 | 8/2012 | Richer et al. | |
| 2013/0095172 A1* | 4/2013 | Alavattam ............ | A61K 45/06 424/450 |
| 2013/0224227 A1 | 8/2013 | Beusker et al. | |
| 2015/0216844 A1 | 8/2015 | Beusker et al. | |
| 2016/0052880 A1 | 2/2016 | Beusker et al. | |

FOREIGN PATENT DOCUMENTS

| | | |
|---|---|---|
| EP | 0 263 526 A1 | 4/1988 |
| EP | 0 154 445 B1 | 5/1989 |
| EP | 0 656 360 A1 | 6/1995 |
| EP | 0 702 014 A1 | 3/1996 |
| EP | 0359454 B1 | 12/2000 |
| EP | 2 380 909 A1 | 10/2011 |
| JP | H 06-56697 A | 3/1994 |
| JP | H 11-500427 A | 1/1999 |
| JP | 2000-511893 A | 9/2000 |
| JP | 2004-518678 A | 6/2004 |
| JP | 2005-532287 A | 10/2005 |
| JP | 2008-517905 A | 5/2008 |
| JP | 2008-531542 A | 8/2008 |
| JP | 2009-529030 A | 8/2009 |
| WO | WO 96/23497 A1 | 8/1996 |
| WO | WO 97/44000 A2 | 11/1997 |
| WO | WO 98/11101 A2 | 3/1998 |
| WO | WO 98/25900 A1 | 6/1998 |
| WO | WO 99/31120 A1 | 6/1999 |

(Continued)

OTHER PUBLICATIONS

El-Sahwi et al. ("El-Sahwi", Expert. Rev. Anticancer Ther., 2002, 12, 1-10).*
Amsellem-Ouazana, D., et al., "Management of Primary Resistance to Gemcitabine and Cisplatin (G—C) Chemotherapy in Metastatic Bladder Cancer With Her2 Over-Expression," *Ann. Oncol.*, 15(3): 538, Kluwer Academic Publishers, United States (2004).
Bartlett, J.M.S., et al., "Type I Receptor Tyrosine Kinases Are Associated With Hormone Escape in Prostate Cancer," *J. Pathol.*, 205: 522-529, John Wiley and Sons Ltd., England (2005).
Beckhardt, R.N., et al., "HER-2/neu Oncogene Characterization in Head and Neck Squamous Cell Carcinoma," *Arch. Otolaryngol. Head Neck Surg.* 121:1265-1270, American Medical Association, United States (1995).
Berchuck, A., et al., "Overexpression of HER-2/neu is Associated with Poor Survival in Advanced Epithelial Ovarian Cancer," *Cancer Res.*, 50: 4087-4091, American Association for Cancer Research, United States (1990).

(Continued)

*Primary Examiner* — Peter J Reddig
*Assistant Examiner* — Kauser Akhoon
(74) *Attorney, Agent, or Firm* — Sterne, Kessler, Goldstein & Fox P.L.L.C.

(57) ABSTRACT

The present invention relates to duocarmycin-containing antibody-drug conjugates (ADCs) for use in the treatment of human solid tumors expressing HER2, wherein the human solid tumor expressing HER2 is endometrial cancer, in particular uterine serous carcinoma (USC). In particular, the present invention relates to duocarmycin-containing ADCs for use in the treatment of endometrial cancer, notably USC, with HER2 IHC 2– or 1+ and HER2 FISH negative tumor tissue status.

11 Claims, 3 Drawing Sheets

(56) References Cited

FOREIGN PATENT DOCUMENTS

| WO | WO 01/83448 A2 | 11/2001 |
|---|---|---|
| WO | WO 02/067930 A1 | 9/2002 |
| WO | WO 02/096910 A1 | 12/2002 |
| WO | WO 03/026577 A2 | 4/2003 |
| WO | WO 03/086318 A2 | 10/2003 |
| WO | WO 03/097635 A1 | 11/2003 |
| WO | WO 2004/032828 A2 | 4/2004 |
| WO | WO 2004/069159 A2 | 8/2004 |
| WO | WO 2004/069201 A2 | 8/2004 |
| WO | WO 2004/101767 A2 | 11/2004 |
| WO | WO 2005/032594 A2 | 4/2005 |
| WO | WO 2005/084390 A2 | 9/2005 |
| WO | WO 2005/112919 A2 | 12/2005 |
| WO | WO 2006/003705 A2 | 4/2006 |
| WO | WO 2007/038658 A2 | 4/2007 |
| WO | WO 2007/051081 A1 | 5/2007 |
| WO | WO 2007/089149 A2 | 8/2007 |
| WO | WO 2008/074004 A2 | 6/2008 |
| WO | WO 2008/103693 A2 | 8/2008 |
| WO | WO 2009/017394 A1 | 2/2009 |
| WO | WO 2009/064908 A1 | 5/2009 |
| WO | WO 2009/064913 A1 | 5/2009 |
| WO | WO 2010/027280 A1 | 3/2010 |
| WO | WO 2010/033733 A1 | 3/2010 |
| WO | WO 2010/062171 A2 | 6/2010 |
| WO | WO 2011/133039 A2 | 10/2011 |
| WO | WO 2012/143523 A1 | 10/2012 |
| WO | WO 2013/049410 A1 | 4/2013 |
| WO | WO 2013/121175 A1 | 8/2013 |
| WO | WO 2015/104359 A2 | 7/2015 |
| WO | WO 2015/104385 A2 | 7/2015 |

OTHER PUBLICATIONS

Bertotti, A., et al., "A Molecularly Annotated Platform of Patient-Derived Xenografts ("Xenopatients") Identifies HER2 as an Effective Therapeutic Target in Cetuximab-Resistant Colorectal Cancer," *Cancer Discov.* 1(6): 508-523, American Association for Cancer Research, United States (2011).

Boger, D.L. and Johnson. D.S., "CC-1065 and the Duocarmycins: Unraveling the Keys to a New Class of Naturally Derived DNA Alkylating Agents," *Proc. Natl. Acad. Sci.* 92(9): 3642-3649, American Association for the Advancement of Science, United States (1995).

Boger, D.L., et al. "Synthesis and Properties of Substituted CBI Analogs of CC-1065 and the Duocarmycins Incorporating the 7-Methoxy-1,2,9,9a-tetrahydrocyclopropal[c]benz[e]indol-4-one (MCBI) Alkylation Subunit: Magnitude of Electronic Effects on the Functional Reactivity," *Journal of Organic Chemistry* 8;61(5):1710-1729, American Chemical Society, United States (1996).

Braga, D., et al., "Crystal Polymorphism and Multiple Crystal Forms" *Struct. Bond.*, 132: 25-50 Sprimter-Verlag, Germany (2009).

Burris, H. and Storniolo, A.M., "Assessing Clinical Benefit in the Treatment of Pancreas Cancer: Gemcitabine Compared to 5-Fluorouracil," *Eur. J. Cancer* 33(Suppl. 1):S18-S22, Elsevier Science Ltd., England (1997).

Cai, C., et al., "Androgen Receptor Expression in Prostate Cancer Cells is Suppressed by Activation of Epidermal Growth Factor Receptor and ErbB2," *Cancer Res.*, 69(12): 5202-5209, American Association for Cancer Research, United States (2009).

Calikusu, Z., et al., "The Effect of HER2 Expression on Cisplatin-Based Chemotherapy in Advanced Non-Small Cell Lung Cancer Patients," *J. Exp. Clin. Cancer Res.*, 28(1):97, BioMed Central Ltd., England (2009).

Chakravarti, A., et al., "Expression of the epidermal growth factor receptor and Her-2 are predictors of favorable outcome and reduced complete response rates, respectively, in patients with muscle-invading bladder cancers treated by concurrent radiation and cisplatin-based chemotherapy: A report from the Radiation Therapy Oncology Group," *Int. J. Radiation Oncology Biol. Phys.*, 62(2): 309-317, Elsevier, The Netherlands (2005).

Chen, L., et al., "Dual EGFR/HER2 Inhibition Sensitizes Prostate Cancer Cells to Androgen Withdrawal by Suppressing ErbB3," *Clin. Cancer Res.*, 17(19): 6218-28, American Association for Cancer Research, United States (2011).

Chevallier, et al., "Trastuzumab for Treatment of Refractory/Relapsed HER2-Positive Adult B-ALL: Results of a Phase 2 GRAALL Study," *Blood*, 119(11): 2474-7, The American Society of Hematology, United States (2012).

Clark, J., et al., "Phase II Trial of 5-Fluororuacil (5-FU), Leucovorin (LV), Oxaliplatin (Ox), and Trastuzamab (T) for Patients With Metastatic Colorectal Cancer (CRC) Refractory to Initial Therapy," *Proc. Am. Soc. Clin. Oncol.* 22:891-abstr 3584, American Society of Clinical Oncology, United States (2003).

Conroy, T., et al., "Folfirinox Versus Gemcitabine for Metastatic Pancreatic Cancer," *N. Engl. J. Med.* 364(19): 1817-25, Massachusetts Medical Society, United States (2011).

Dokter, W., et al., "Abstract 4329: Novel Her2 Targeting Antibody-Drug Conjugates Based on DNA-Interacting Duocarmycin and an Unique Linker Technology With Great Potential in Breast Cancer and NSCLC," Proceedings of the 104th Annual Meeting of the American Association for Cancer Research; Apr. 6-10, 2013; *Cancer Res* 73(8Suppl):Abstract nr 4329, AACR, United States (2013).

Dokter, W., et al., "Preclinical Profile of the HER2-Targeting ADC SYD983/SYD985: Introduction of a New Duocarmycin-Based Linker-Drug Platform" (Supplemental Data Included) *Molecular Cancer Therapeutics* 13(11):2618-2629, American Association of Cancer Research, United States (Sep. 2014).

Ebb, D., et al., "Phase II Trial of Trastuzumab in Combination With Cytotoxic Chemotherapy for Treatment of Metastatic Osteosarcoma With Human Epidermal Growth Factor Receptor 2 Overexpression: A Report From the Children's Oncology Group," *J. Clin. Oncol.* 30(20): 2545-2551, American Society of Clinical Oncology, United States (2012).

English, D.P., et al., "T-DM1, A Novel Antibody-Drug Conjugate, is Highly Effective Against Primary HER2 Overexpressing Uterine Serous Carcinoma In Vitro and In Vivo," *Cancer Medicine* 3(5): 1256-1265, John Wiley and Sons, United States (Jun. 2014).

Extended European Search Report for EP Application No. EP 14 15 0791, European Patent Office, Germany, mailed on Jun. 30, 2014, 17 pages.

Fiebig et al., "Comparison of Tumor Response in Nude Mice and in the Patients," *Behring Inst. Mitt.* 74: 343-352, Nature Publishing Group, England (1984).

Fiebig, H.H., et al., "Gene Signatures Developed From Patient Tumor Explants Grown in Nude Mice to Predict Tumor Response to 11 Cytotoxic Drugs," *Cancer Genomics & Proteomics* 4: 197-210, International Institute of Anticancer Research, Greece (1997).

Fleming et al.,"Phase II Trial of Trastuzumab in Women with Advanced or Recurrent, HER2-Positive Endometrial Carcinoma: a Gynecologic Oncology Group Study," *Gynecol. Oncol.* 116(1): 15-20, Elsevier Inc., The Netherlands (2010).

Flygare, J.A., et al., "Antibody-Drug Conjugates for the Treatment of Cancer,"*Chemical Biology & Drug Design*, 81(1):113-121, John Wiley & Sons A/S, United States (Jan. 2013).

Gaborit, N., et al., "Time-Resolved Fluorescence Resonance Energy Transfer (TR-FRET) to Analyze the Disruption of EGFR/HER2 Dimers: A New Method to Evaluate the Efficiency of Targeted Therapy Using Monoclonal Antibodies," *J. Biol. Chem.*, 286(13): 11337-11345, American Society for Biochemistry and Molecular Biology, United States (2011).

Garg, K. and Soslow, R.A., "Endometrial Carcinoma in Women Aged 40 Years and Younger,"*Arch. Pathol. Lab. Med.*, 138: 335-342, College of American Pathologists, United States (Mar. 2014).

Gorlick, R., et al., "Expression of HER2/erbB-2 Correlates With Survival in Osteosarcoma," *J. Clin. Oncol*, 17(9):2781-8, American Society of Clinical Oncology, United States (1999).

Hidalgo, et al., "A Pilot Clinical Study of Treatment Guided by Personalized Tumorgrafts in Patients With Advanced Cancer," *Mol. Cancer Ther.* 10(8):1311-1316, American Association for Cancer Research, United States (2011).

(56) References Cited

OTHER PUBLICATIONS

Hsu, F.-N., et al., "The Significance of Her2 on Androgen Receptor Protein Stability in the Transition of Androgen Requirement in Prostate Cancer Cells," *Am. J. Physiol. Endocrinol. Metab.*, 300:E902-E908, American Physiological Society, United States (2011).

Hussain, M.H.A., et al., "Trastuzumab, Paclitaxel, Carboplatin, and Gemcitabine in Advanced Human Epidermal Growth Factor Receptor-2/neu-Positive Urothelial Carcinoma: Results of a Multicenter Phase II National Cancer Institute Trial," *J. Clin. Oncol.*, 25(16):2218-24, American Society of Clinical Oncology, United States (2007).

International Search Report and Written Opinion for International Application No. PCT/EP2015/050332, European Patent Office, Netherlands, mailed on Jul. 20, 2015, 15 Pages.

International Search Report and Written Opinion for International Application No. PCT/EP2015/050350, European Patent Office, Netherlands, mailed on Jul. 6, 2015, 14 Pages.

Irwin, M.E., et al., "Small Molecule ErbB Inhibitors Decrease Proliferative Signaling and Promote Apoptosis in Philadelphia Chromosome-Positive Acute Lymphoblastic Leukemia," PLoS ONE, 8(8): e70608, Public Library of Science, United States (2013).

Jewell, E. et al., "Use of Trastuzumab in the Treatment of Metastatic Endometrial Cancer" *Int. J. Gynecol. Cancer 16*: 1370-1373, Lippincott Williams & Wilkins, United States (2006).

Kazane, S. A., et al.,"Site-Specific DNA-Antibody Conjugates for Specific and Sensitive Immuno-PCR," *Proceedings of the National Academy of Sciences*, 109(10):3731-3736, United States National Academy of Sciences, United States (2012).

Kelly, R.K., et al., "An Antibody-Cytotoxic Conjugate, BIIB015, Is a New Targeted Therapy for Cripto Positive Tumours," *European Journal of Cancer 47*(11):1736-1746, Pergamon Press, England (2011).

Kutty, R.V., et al., "Cetuximab Conjugated Vitamine E TPGS Micelles for Targeted Delivery of Docetaxel for Treatment of Triple Negative Breast Cancers," *Biomaterials*, 34(38):10160-10171, Elsevier Science, The Netherlands (2013).

Langdon, S.P., et al., "Pertuzumab for the treatment of ovarian cancer," *Expert Opin. Biol. Ther. 10*(7): 1113-1120, Informa UK Ltd., England (2010).

Larbouret, C., et al., "In Pancreatic Carcinoma, Dual EGFR/HER2 Targeting with Cetuximab/Trastuzumab is More Effective than Treatment with Trastuzumab/Erlotinib or Lapatinib Alone: Implication of Receptors' Down-regulation and Dimers' Disruption," *Neoplasia 14*(2): 121-130, Elsevier, The Netherlands (2012).

Makhija, S., et al., "Clinical Activity of Gemcitabine Plus Pertuzumab in Platinum-Resistant Ovarian Cancer, Fallopian Tube Cancer, or Primary Peritoneal Cancer," *J. Clin. Oncol.*, 28(7): 1215-1223, American Society of Clinical Oncology, United States (2010).

Mantia-Smaldone, G.M., et al., "Targeted treatment of recurrent platinum-resistant ovarian cancer: current and emerging therapies," *Cancer Management Res. 3*: 25-38, Dove Medical Press Ltd., England (2011).

Mazières, J., et al., "Lung Cancer That Harbors an HER2 Mutation: Epidemiologic Characteristics and Therapeutic Perspectives," *J. Clin. Oncol.*, 31(16): 1997-2003, American Society of Clinical Oncology, United States (2013).

Meden, H. and Kuhn, W., "Overexpression of the oncogene c-erbB-2 (HER2/neu) in ovarian cancer: a new prognostic factor," *Eur. J. Obstet. & Gynecol. Reprod. Biol.*, 71: 173-179, Elsevier, The Netherlands (1997).

Minner, S., et al., "Low level HER2 Overexpression is Associated With Rapid Tumor Cell Proliferation and Poor Prognosis in Prostate Cancer," *Clin. Cancer Res.*, 16(5): 1553-60, American Association for Cancer Research, United States (2010).

National Comprehensive Cancer Network (NCCN), NCCN Guidelines®, Version 2.2015, Uterine Neoplasms, Accessed at http://www.nccn.org/professionals/physician_gls/PDF/uterine.pdf on Sep. 15, 2015.

Nolting, B., "Linker Technologies for Antibody-Drug Conjugates," *Methods in Molecular Biology—Antibody-Drug Conjugates 1045*:71-100, Humana Press, United States (2013).

Popowycz, F. et al., "Synthesis and reactivity of 4-, 5- and 6-azaindoles," *Tetrahedron 63*(36): 8689-8707, Elsevier Ltd., The Netherlands (2007).

Ramanathan, R.K., et al., "Low Overexpression of HER-2/PPPNeu in Advanced Colorectal Cancer Limits the Usefulness of Trastuzumab (Herceptin®) and Irinotecan as Therapy. A Phase II Trial," *Cancer Invest. 22*(6): 858-865, Marcel Dekker, United States (2004).

Ray-Coquard, I., et al., "HER2 Overexpression/Amplification and Trastuzumab Treatment in Advanced Ovarian Cancer: A GINECO Phase II Study," *Clin. Ovarian Cancer*, 1(1): 54-59, Elsevier, The Netherlands (2008).

Santin, A.D., et al., "Overexpression of HER-2/Neu in Uterine Serous Papillary Cancer," *Clin. Cancer Res.*, 8: 1271-1279, American Association for Cancer Research, United States (2002).

Santin, A.D., et al., "Trastuzumab Treatment in Patients With Advanced or Recurrent Endometrial Carcinoma Overexpressing HER2/neu," *Int. J. Gynecol. Obstet. 102*: 128-131, Elsevier Ireland Ltd., The Netherlands (2008).

Scholl, S., et al., "Targeting HER2 in Other Tumor Types," *Ann. Oncol.*, 12(Suppl. 1):S81-S87. Kluwer Academic Publishers, The Netherlands (2001).

Seo, A.N., et al., "HER2 Status in Colorectal Cancer: Its Clinical Significance and the Relationship between HER2 Gene Amplification and Expression," *PLoS ONE*, 9(5): e98528, Public Library of Science, United States (May 2014).

Shariat, S.F., et al., "Preoperative Plasma HER2 and Epidermal Growth Factor Receptor For Staging and Prognostication in Patients with Clinically Localized Prostate Cancer," *Clin. Cancer Res.*, 13(18): 5377-84, American Association for Cancer Research, United States (2007).

Shen, B-Q., et al., "Conjugation Site Modulates the In Vivo Stability and Therapeutic Activity of Antibody-Drug Conjugates," *Nature Biotechnology 30*(2):184-189, Nature Publishing Group, United States (2012).

Shigematsu, H., et al., "A Case of HER-2-Positive Recurrent Breast Cancer Showing a Clinically Complete Response to Trastuzumab-Containing Chemotherapy After Primary Treatment of Triple-Negative Breast Cancer," *World Journal of Surgical Oncolology 9*:146, Biomed Central Ltd., England (2011).

Slomovitz, B.M., et al., "Her-2/neu Overexpression and Amplification in Uterine Papillary Serous Carcinoma," *J. Clin. Oncol. 22*(15): 3126-3132, American Society of Clinical Oncology, United States (2004).

Suzuki, M., et al., "HER2 gene mutations in non-small cell lung carcinomas: Concurrence with her2 gene amplification and her2 protein expression and phosphorylation," *Lung Cancer.* 87(1):14-22, Elsevier Ireland Ltd., The Netherlands (Jan. 2015).

Synthon, "Synthon Biopharmaceuticals reports positive early results with its second generation HER2-antibody-drug conjugate", Jan. 22, 2013, Accessed at http://www.synthon.com/Corporate/News/PressReleases/Synthon-reports-positive-early-results-with-its-second-generation-HER2-antibody-drug-conjugate.aspx on Sep. 1. 2015.

Takezawa, K., et al.,"HER2 amplification: a potential mechanism of acquired resistance to EGFR inhibition in EGFR-mutant lung cancers that lack the second-site EGFRT790M mutation," *Cancer Discov. 2*(10): 922-33, American Association for Cancer Research, United States (2012).

Tietze et. al. "Determination of the Biological Activity and Structure Activity Relationships of Drugs Based on the Highly Cytotoxic Duocarmycins and CC-1065," *Toxins 1*: 134-150, MDPI AG, Switzerland (2009).

Trail, P. A., "Antibody Drug Conjugates As Cancer Therapeutics", *Antibodies 2*(1):113-129, MDPI AG, Switzerland (Feb. 2013).

(56) References Cited

OTHER PUBLICATIONS

Tsai, C.-M., et al., "Correlation of Intrinsic Chemoresistance of Non-Small-Cell Lung Cancer Cell Lines With HER-2/neu Gene Expression but Not With ras Gene Mutations," *J. Natl. Cancer Inst.*, 85(11): 897-901, Oxford University Press, England (1993).

Vippagunta et al. "Crystalline Solids," *Advanced Drug Delivery Reviews* 48(1): 3-26, Elsevier Science B.V., The Netherlands (2001).

Website: Champions Oncology, "Predictive value" Accessed at http://web.archive.org/web/20111204221017/http://www.championsoncology.com/translationaloncologysolutions/predictivevalue on Sep. 15, 2015.

Non-Final Office Action in U.S. Appl. No. 12/671,609, inventors Beusker, P., et al., filed Oct. 26, 2010, pp. 1-13, U.S. Patent Office, United States, mailed Oct. 24, 2012.

Final Office Action in U.S. Appl. No. 12/671,609, inventors Beusker, P., et al., filed Oct. 26, 2010, pp. 1-13, U.S. Patent Office, United States, mailed May 8, 2013.

Notice of Allowance in U.S. Appl. No. 12/671,609, inventors Beusker, P., et al., filed Oct. 26, 2010, pp. 1-15, U.S. Patent Office, United States, mailed Nov. 6, 2013.

Non-Final Office Action in U.S. Appl. No. 13/126,920, inventors Beusker, P., et al., filed Apr. 29, 2011, pp. 1-20, U.S. Patent Office, United States, mailed Apr. 22, 2013.

Final Office Action in U.S. Appl. No. 13/126,920, inventors Beusker, P., et al., filed Apr. 29, 2011, pp. 1-22, U.S. Patent Office, United States, mailed Jan. 7, 2014.

Notice of Allowance in U.S. Appl. No. 13/126,920, inventors Beusker, P., et al., filed Apr. 29, 2011, pp. 1-5, U.S. Patent Office, United States, mailed Jul. 7, 2014.

Non-Final Office Action in U.S. Appl. No. 13/642,847, inventors Beusker, P., et al., filed Nov. 27, 2012, pp. 1-23, U.S. Patent Office, United States, mailed Mar. 20, 2015.

English language translation of WO 98/25900 (cited as document FP2 on accompanying form PTO/SB/08A). Google translate, Apr. 30, 2013.

Final Office Action in U.S. Appl. No. 13/642,847, inventors Beusker, P. et al., filed Nov. 27, 2012, 18 pages, U.S. Patent Office, United States, mailed Dec. 2, 2015.

Amishiro, N. et al., "New Water-Soluble Duocarmycin Derivatives: Synthesis and Antitumor Activity of A-Ring Pyrrole Compounds Bearing β-Heteroarylacryloyl Groups," *Journal of Medicinal Chemistry* 42(4):669-676, American Chemical Society, United States (1999).

Amishiro, N. et al., "Synthesis and Antitumor Activity of Duocarmycin Derivatives: A-Ring Pyrrole Compounds Bearing β-(5',6',7'-Trimethoxy-2'-indolyl)acryloyl Group," *Bioorganic & Medicinal Chemistry* 8(7):1637-1643, Elsevier Science Ltd., England (2000).

Atwell, G.J. et al., "5-Amino-1-(chloromethyl)-1,2-dihydro-3H-benz[e]indoles: Relationships between Structure and Cytotoxicity for Analogues Bearing Different DNA Minor Groove Binding Subunits," *Journal of Medicinal Chemistry* 42(17):3400-3411, American Chemical Society, United States (1999).

Boger, D.L. et al., "Synthesis and Evaluation of a Series of C3-Substituted CBI Analogues of CC-1065 and the Duocarmycins," *The Journal of Organic Chemistry* 66(15):5163-5173, American Chemical Society, United States (2001).

Jeffrey, S.C. et al., "Design, Synthesis, and in Vitro Evaluation of Dipeptide-Based Antibody Minor Groove Binder Conjugates," *Journal of Medicinal Chemistry* 48(5):1344-1358, American Chemical Society, United States (2005).

Parrish, J.P. et al., "Establishment of Substituent Effects in the DNA Binding Subunit of CBI Analogues of the Duocarmycins and CC-1065," *Bioorganic & Medicinal Chemistry* 11(17):3815-3838, Elsevier Ltd., England (2003).

Parrish, J.P. et al., "Synthesis and Evaluation of N-aryl and N-alkenyl CBI Derivatives," *Bioorganic & Medicinal Chemistry* 12(22):5845-5856, Elsevier Ltd., England (2004).

Schuster, H.J. et al., "Synthesis of the First Spacer Containing Prodrug of a Duocarmycin Analogue and Determination of Its Biological Activity," *Organic & Biomolecular Chemistry* 8(8):1833-1842, Royal Society of Chemistry, England (2010).

Tietze, L.P. et al., "A Strategy for Tumor-Selective Chemotherapy by Enzymatic Liberation of seco-duocarmycin SA-Derivatives from Nontoxic Prodrugs," *Bioorganic & Medicinal Chemistry* 9:1929-1939, Elsevier Science Ltd., England (2001).

Tietze, L.F. et al., "Highly Selective Glycosylated Prodrugs of Cytostatic CC-1065 Analogues for Antibody-Directed Enzyme Tumor Therapy," *ChemBioChem* 2(10):758-765, Wiley-VCH-Verlag GmbH, Germany (2001).

Tietze, L.F. et al., "Synthesis and Biological Evaluation of Novel Analogues and Prodrugs of the Cytotoxic Antibiotic CC-1065 for Selective Cancer Therapy," *European Journal of Organic Chemistry* 10:1634-1645, Wiley-VCH Verlag GmbH, Germany (2002).

Tietze, L.F. et al., "Antitumor Agents: Development of Highly Potent Glycosidic Duocarmycin Analogues for Selective Cancer Therapy," *Angewandte Chemie International Edition* 45:6574-6577, Wiley-VCH Verlag GmbH & Co. KGaA, Germany (2006).

Tietze, L.F. et al., "Selective Treatment of Cancer: Synthesis, Biological Evaluation and Structural Elucidation of Novel Analogues of the Antibiotic CC-1065 and the Duocarmycins," *Chemistry—A European Journal* 13(16):4396-4409, Wiley-VCH Verlag GmbH, Germany (2007).

Tietze, L.F. et al., "Asymmetric Synthesis and Biological Evaluation of Glycosidic Prodrugs for a Selective Cancer Therapy," *ChemMedChem* 3(12):1946-1955, Wiley-VCH Verlag GmbH & Co. KGaA, Germany (2008).

Wang, Y. et al., "Design, Synthesis, Cytotoxic Properties and Preliminary DNA Sequencing Evaluation of CPI—N-methylpyrrole Hybrids. Enhancing Effect of a trans Double Bond Linker and Role of the Terminal Amide Functionality on Cytotoxic Potency," *Anti-Cancer Drug Design* 11(1):15-34, Oxford University Press, United States (1996).

Wang, Y. et al, "CC-1065 Analogues Bearing Different DNA-Binding Subunits: Synthesis, Antitumor Activity, and Preliminary Toxicity Study," *Journal of Medicinal Chemistry* 46(4):634-637, American Chemical Society, United States (2003).

Cumnock, K., et al., "Trisulfide Modification Impacts the Reduction Step in Antibody-Drug Conjugation Process," *Bioconjugate Chemistry* 24(7):1154-1160, American Chemical Society, United States (2013).

Dokter, W.H.A., et al., "Abstract 2652: In vitro and in vivo antitumor activity of SYD985, a novel HER2-targeting ADC: a comparison with T-DM1," *Cancer Research* 74(Suppl 19):Abstract 2652, Proceedings of the 105$^{th}$ Annual Meeting of the American Association for Cancer Research, Apr. 5-9, 2014, San Diego, CA (Oct. 1, 2014).

Foulkes, W.D., et al., "Triple-Negative Breast Cancer," *The New England Journal of Medicine* 363:1938-1948, Massachusetts Medical Society, United States (2010).

Hamblett, K.J., et al., "Effects of Drug Loading on the Antitumor Activity of a Monoclonal Antibody Drug Conjugate," *Clinical Cancer Research* 10(20):7063-7070, American Association for Cancer, United States (2004).

Kovtun, Y.V. and Goldmacher, V.S., "Cell killing by antibody-drug conjugates," *Cancer Letters* 255(2):232-240, Elsevier Ireland Ltd., Ireland (2007).

McDonagh, C.F., et al., "Engineered antibody-drug conjugates with defined sites and stoichiornetries of drug attachment," *Protein Engineering, Design & Selection* 19(7):299-307, Oxford University Press, England (2006).

Müller, U., "Polymorphism," in *Inorganic Structural Chemistry*, pp. 14-15, John Wiley & Sons Ltd, England (1993).

Ouyang, J., "Drug-to-antibody ratio (DAR) and drug load distribution by hydrophobic interaction chromatography and reversed phase high-performance liquid chromatography," *Methods in Molecular Biology* 1045:275-283, Springer Science+Business Media, LLC, England (2013).

(56) References Cited

OTHER PUBLICATIONS

Sun, M.M.C., et al., "Reduction-Alkylation Strategies for the Modification of Specific Monoclonal Antibody Disulfides," *Bioconjugate Chem.* 16(5):1282-1290, American Chemical Society, United States (2005).

Greenwald, R.B., et al., "Effective drug delivery by PEGylated drug conjugates,"*Advanced Drug Delivery Reviews* 55(2):217-250, Elsevier Science B.V., Netherlands (2003).

Van Der Lee, M., et al., "Poster 2652:The HER2-targeting ADC SYD985 shows superior antitumor activity compared to T-DM1 in preclinical studies with an activity profile that includes low-HER2 expressing breast cancers," AACR Annual Meeting 2014, Apr. 5-9, 2014, San Diego, CA.

Van Der Lee, M.M., et al., "The Preclinical Profile of the Duocarmycin-Based HER2-Targeting ADC SYD985 Predicts for Clinical Benefit in Low HER2-Expressing Breast Cancers," *Mol Cancer Ther.* 14(3):692-703, American Association for Cancer Research, United States (published online Jan. 14, 2015).

Verheijden, G., et al., "Poster 850294: Preclinical Data of SYD985 Support the Clinical Investigation of This Novel Anti-HER2 Antibody-Drug Conjugate in Breast Cancer Patients with Low Levels of HER2 Expression," 2014 San Antonio Breast Cancer Symposium, (Dec. 2014).

International Search Report and Written Opinion for International Application No. PCT/EP2015/050304, European Patent Office, Rijswijk, Netherlands, mailed on Jul. 10, 2015, 12 pages.

Non-Final Office Action mailed Dec. 18, 2015 in U.S. Appl. No. 14/174,794, inventors Beusker, P.H. et al., filed Feb. 6, 2014.

Non-Final Office Action mailed Mar. 16, 2016 in U.S. Appl. No. 14/859,201, inventors Dokter, W. et al., § 371(c) date Sep. 18, 2015.

Non-Final Office Action mailed Jun. 2, 2016 in U.S. Appl. No. 14/526,462, inventors Beusker, P.H. et al., filed Oct. 28, 2014.

Non-Final Office Action mailed Jun. 2, 2016 in U.S. Appl. No. 13/642,847, inventors Beusker, P.H. et al., filed Nov. 27, 2012.

\* cited by examiner

DUOCARMYCIN ADCS FOR USE IN TREATMENT OF ENDOMETRIAL CANCER

FIELD OF THE INVENTION

The present invention relates to duocarmycin antibody-drug conjugates (ADCs) showing improved in vivo antitumor activity, in particular duocarmycin ADCs for use in the treatment of endometrial cancer. More in particular, the present invention relates to duocarmycin-containing ADCs for use in the treatment of human solid tumours expressing human epidermal growth factor receptor 2 (HER2), wherein the human solid tumour expressing HER2 is endometrial cancer, particularly wherein the human solid tumour expressing HER2 is uterine serous carcinoma (USC).

BACKGROUND OF THE PRESENT INVENTION

Endometrial (uterine) cancer is the most common gynaecological malignancy in Europe and North America. It is the seventh most common cause of death from cancer in women in Western-Europe, accounting for 1%-2% of all deaths from cancer. According to the most recent NCCN guidelines, pathologist review differentiates uterine cancer in three distinct types: i) pure endometrioid carcinoma, ii) serous or clear cell adenocarcinoma, and iii) carcinosarcoma, i.e. a mixed type of carcinoma and sarcoma (NCCN Guidelines®, Version 2.2015). The distinction between endometrioid and serous carcinomas of the endometrium is important for prognostic and therapeutic purposes. Endometrioid carcinomas typically are confined to the uterus and have better prognosis than endometrial serous carcinomas that have frequent peritoneal dissemination and a worse prognosis (K. Garg and R. A. Soslow in Arch. Pathol. Lab. Med., Vol. 138, March 2014, 335-342).

Uterine serous carcinoma (USC), or uterine papillary serous carcinoma, accounts for approx. 10% of endometrial cancer. This subtype of endometrial cancer is biologically highly aggressive and causes the most endometrial cancer deaths. Molecular profiling studies have demonstrated HER2 to be one of the most over-expressed genes in USC. HER2 is a member of the epidermal growth factor receptor (EGFR) family of receptor tyrosine kinases. HER2 over-expression has been reported to range from 18% to 80% in USC due to several factors like tumour type and stage of the tissue sample as well as the immunohistochemistry (IHC) technique used (A. D. Santin et al. in Clin. Cancer Res., 8, 2002, 1271-1279; B. M. Slomovitz et al. in J. Clin. Oncol. 22, 2004, 3126-3132). Up to 35% of USCs may over-express the HER2 oncogene at high level by immunohistochemistry (i.e. HER2 IHC 3+) or harbour HER2 gene amplification by fluorescence in situ hybridization (i.e. FISH positive). An additional 45% of USCs express HER2 at moderate (i.e. HER2 IHC 2+) or low (i.e. HER2 IHC 1+) levels.

Trastuzumab (Herceptin™, Genentech/Roche) is a recombinant humanized IgG1 monoclonal antibody against the extracellular domain of HER2 and is currently approved for the treatment of both metastatic and early-stage breast cancer as well as locally advanced or metastatic gastric cancer over-expressing HER2. Case study reports describe the use of trastuzumab in endometrial cancer. In the Int. J. Gynecol. Cancer 16: 1370-1373, 2006, E. Jewell et al. describe a positive result of the administration of trastuzumab to one patient with metastatic endometrial cancer. In the Int. J. Gynecol. Obstet. 102: 128-131, 2008, A. D. Santin et al. report the results of treatment with trastuzumab in two patients with advanced or recurrent endometrial carcinoma that over-express HER2, In Gynecol. Oncol. 116: 15-20, 2010, Fleming et al. report results of a Phase II trial of 34 patients who had HER2-positive endometrial carcinoma and were treated with trastuzumab. Trastuzumab has not currently been approved for the treatment of any endometrial cancer.

D. P. English et al. report in Cancer Medicine published by John Wiley & Sons Ltd., pp. 1-10, 2014, that T-DM1 is highly effective against primary HER2 over-expressing uterine serous carcinoma (USC) in vitro and in vivo. T-DM1 (Kadcyla™, ado-trastuzumab emtansine, Genentech/Roche) is an antibody-drug conjugate which comprises trastuzumab covalently linked to the anti-microtubule agent DM1. DM1 belongs to the maytansine class of chemotherapeutic agents. On average, 3-4 molecules of DM1 are conjugated to each trastuzumab molecule. T-DM1 is an agent aimed at delivering the highly potent DM1 into HER2 over-expressing cells via receptor-mediated endocytosis. T-DM1 has been approved for the treatment of patients with HER2-positive metastatic breast cancer who received prior treatment with trastuzumab and a taxane. The authors conclude that T-DM1 shows promising antitumor effect in HER2-positive USC cell lines and USC (i.e. HER2 IHC 3+) xenografts in SCID mice (15 mg/kg, i.p. injections once per week) and its activity is significantly higher when compared to trastuzumab, and that T-DM1 may represent a novel treatment option for HER2-positive USC patients with disease refractory to standard chemotherapy. No clinical investigations are currently ongoing with T-DM1 for the treatment of endometrial cancer.

BRIEF DESCRIPTION OF THE PRESENT INVENTION

The present invention relates to duocarmycin-containing ADCs for use in the treatment of human solid tumours expressing HER2, wherein the human solid tumour expressing HER2 is endometrial cancer, particularly wherein the human solid tumour expressing HER2 is USC.

DETAILED DESCRIPTION OF THE PRESENT INVENTION

Figure 1:
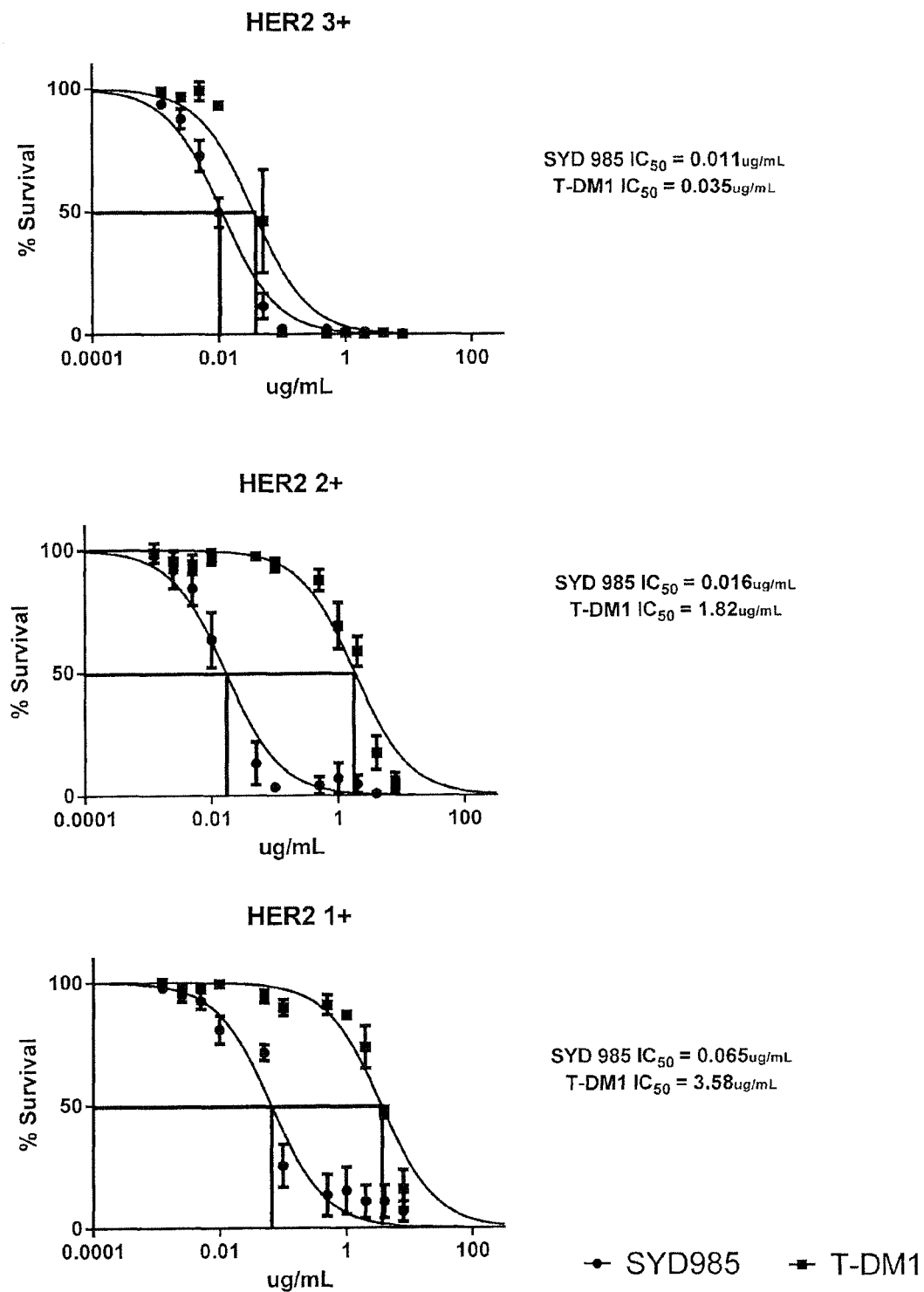
FIG. 1. In vitro USC cell line cytotoxicity: SYD985 versus T-DM1.

The present invention relates to duocarmycin-containing ADCs for use in the treatment of human solid tumours expressing HER2 (i.e. HER2 IHC 3+, 2+ or 1+), wherein the human solid tumour expressing HER2 is endometrial cancer, particularly wherein the human solid tumour expressing HER2 is USC.

In one embodiment, the present invention provides a compound of formula (I)

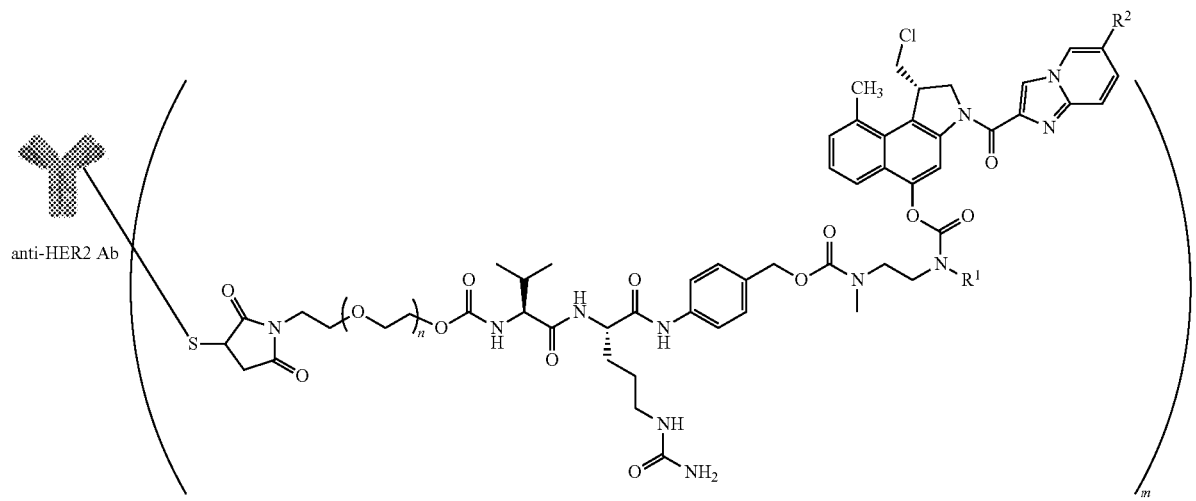

wherein anti-HER2 Ab is an anti-HER2 antibody or antibody fragment, n is 0-3, preferably 0-1, m represents an average DAR of from 1 to 4, $R^1$ is selected from

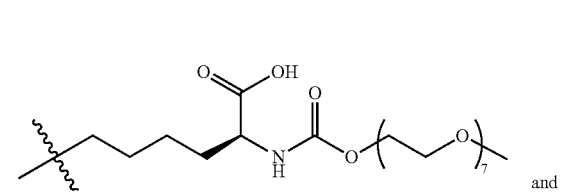

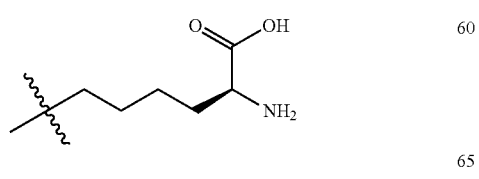

y is 1-16, and $R^2$ is selected from

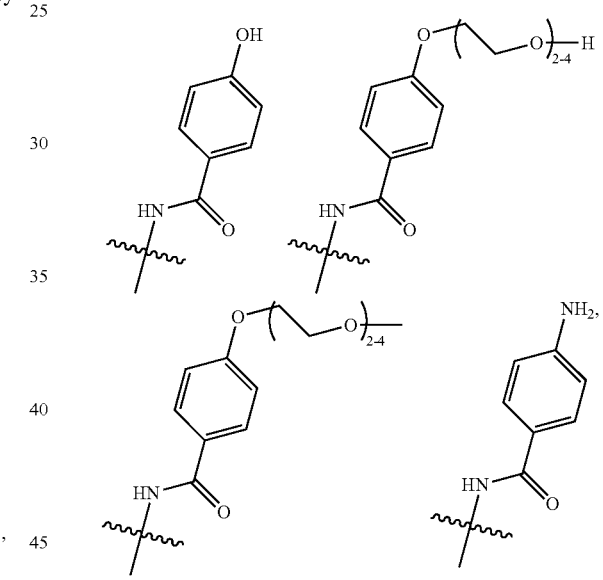

for use in the treatment of human solid tumours expressing HER2, wherein the human solid tumour expressing HER2 is endometrial cancer, particularly wherein the human solid tumour expressing HER2 is USC.

In another embodiment, the present invention relates to a compound of formula (I), wherein anti-HER2 Ab is an anti-HER2 antibody or antibody fragment, n is 0-1, m represents an average DAR of from 1 to 4, preferably from 2 to 3, $R^1$ is selected from

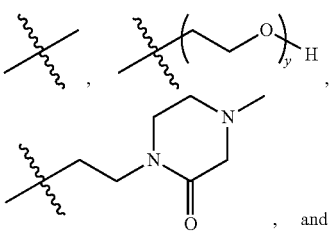

, and

-continued

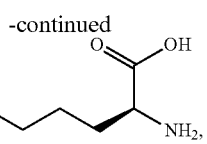

y is 1-16, preferably 1-4, and $R^2$ is selected from

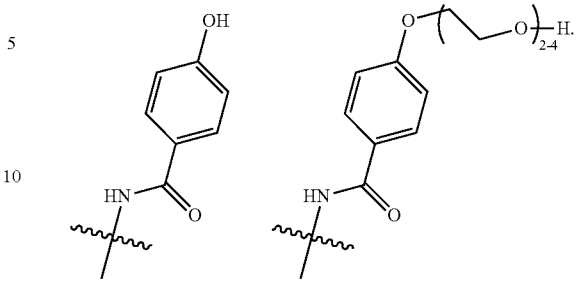

In a further embodiment, the present invention relates to a compound of formula (I), wherein the anti-HER2 Ab is an anti-HER2 monoclonal antibody, n is 0-1, m represents an average DAR of from 2 to 3, preferably from 2.5 to 2.9, $R^1$ is selected from

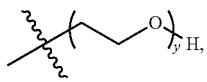

y is 1-4, and $R^2$ is selected from

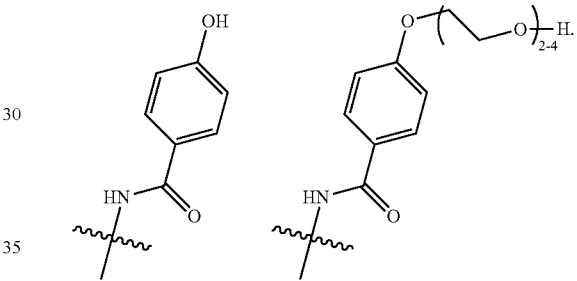

In yet another embodiment, the present invention relates to a compound of formula (I), wherein the anti-HER2 Ab is trastuzumab or a biosimilar thereof, n is 0-1, m represents an average DAR of from 2 to 3, preferably 2.5 to 2.9, $R^1$ is selected from

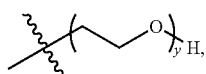

y is 1-4, and $R^2$ is selected from

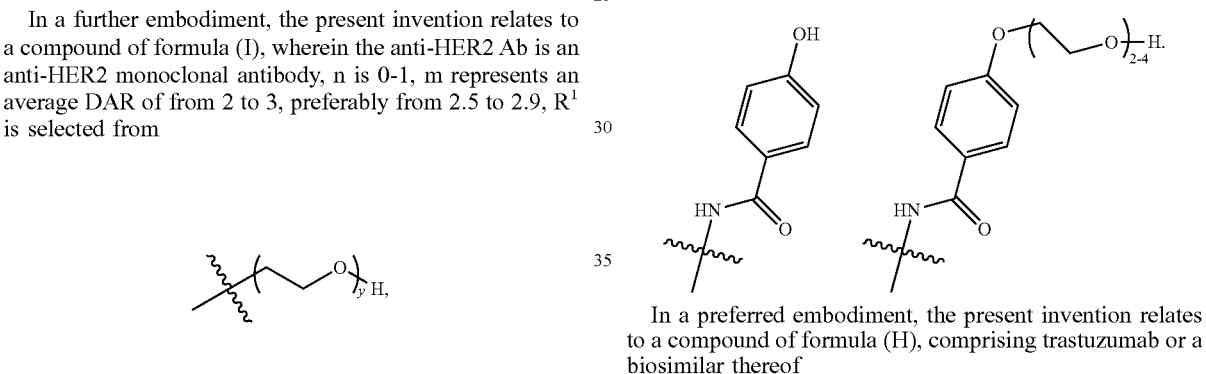

In a preferred embodiment, the present invention relates to a compound of formula (H), comprising trastuzumab or a biosimilar thereof

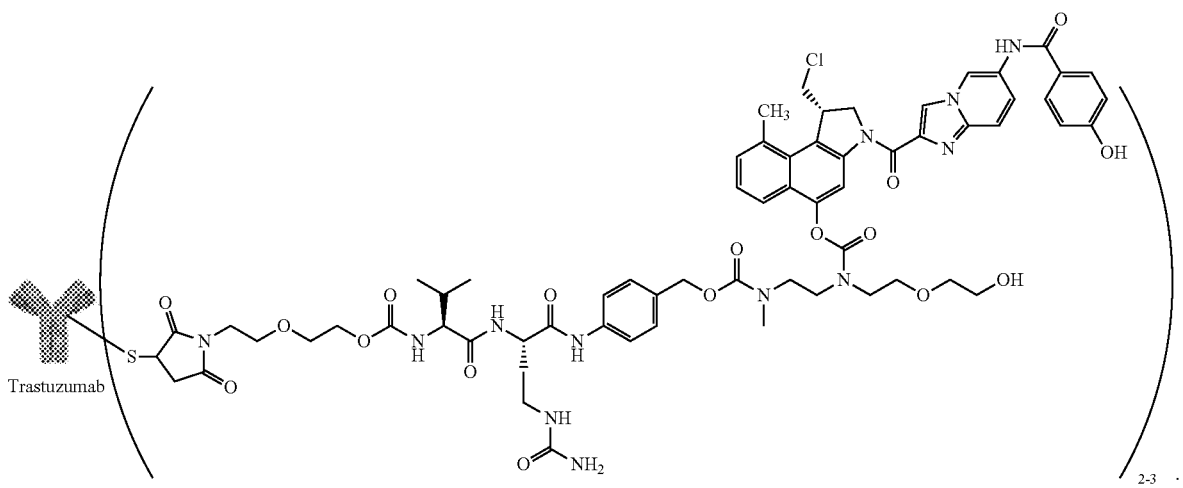

The compound of formula (II) that is referred to as SYD985 in the present specification has an average DAR of from 2.6 to 2.9.

In the structural formulae shown in the present specification, n represents an integer from 0 to 3, while m represents an average drug-to-antibody ratio (DAR) of from 1 to 4. As is well-known in the art, the DAR and drug load distribution can be determined, for example, by using hydrophobic interaction chromatography (HIC) or reversed phase high-performance liquid chromatography (RP-HPLC). HIC is particularly suitable for determining the average DAR.

Duocarmycins, first isolated from a culture broth of *Streptomyces* species, are members of a family of antitumor antibiotics that include duocarmycin A, duocarmycin SA, and CC-1065. These extremely potent agents allegedly derive their biological activity from an ability to sequence-selectively alkylate DNA at the N3 position of adenine in the minor groove, which initiates a cascade of events leading to tumour cell death.

WO2011/133039A discloses a series of analogues of the DNA-alkylating agent CC-1065 and HER2 targeting antibody-drug conjugates (ADCs) thereof. In Example 15, a number of trastuzumab-duocarmycin conjugates were tested against N87 (i.e. HER2 IHC 3+ gastric tumour) xenografts in nude mice.

Typical examples of endometrial (uterine) cancer which can be treated in accordance with the present invention include endometrioid carcinoma, serous or clear cell adenocarcinoma, and carcinosarcoma. Advantageously, the endometrial cancer is USC.

In one embodiment, the present invention provides a compound of formula (I) or (II) for use in the treatment of endometrial cancer showing moderate or low expression of HER2 (i.e. HER2 IHC 2+ or 1+), in particular USC.

In another embodiment, the present invention provides a compound of formula (I) or (II) for use in the treatment of endometrial cancer without HER2 gene amplification (i.e. HER2 FISH negative), in particular USC.

Unexpectedly, the present inventors have found that the compounds of the present invention particularly can be used for the treatment of endometrial cancer, especially USC, with a moderate or low expression of HER2 (i.e. HER2 IHC 2+ or 1+) and/or without HER2 gene amplification (i.e. HER2 FISH negative). Neither trastuzumab nor T-DM1 showed efficacy against such tumours. WO2011/133039A does not teach or suggest the use of duocarmycin-containing ADCs for use in the treatment of endometrial cancer either.

In an advantageous embodiment of the present invention the endometrial cancer is USC showing moderate or low HER2 expression (i.e. HER2 IHC 2+ or 1+) without HER2 gene amplification (i.e. HER2 FISH negative).

Typically, the antitumor activity is evaluated first in (human) tumour cell lines in vitro followed by evaluation in vivo. The antitumor activity of the ADCs falling within the scope of the present invention advantageously is evaluated in animal models, typically nude mice bearing a subcutaneous xenograft. The xenograft can either be a (human) tumour cell line or a patient-derived (primary) tumour.

In accordance with the present invention, the anti-HER2 antibody or antibody fragment can be any antibody or antibody fragment able to bind HER2, e.g. an IgG1 antibody having the complementary determining regions (CDRs) of trastuzumab or an antibody that shows competitive binding with trastuzumab. A preferred antibody is a monoclonal anti-HER2 antibody. A particularly preferred monoclonal antibody is trastuzumab or a biosimilar thereof.

Antibody-drug conjugate (ADC) compounds of formula (I) and (II) in accordance with the present invention have the linker-drug conjugated to the antibody through the S-atom of a cysteine residue, i.e. they are cysteine-linked antibody-drug conjugates. The cysteine residue can either be a natural cysteine residue which is present in the heavy and/or light chain of the antibody (Ab) and forms inter-chain disulfide bonds, or an engineered cysteine residue which is introduced into the Ab at one or more suitable positions in the heavy and/or light chain. The present invention is particularly drawn to ADC compounds wherein the linker-drug is conjugated through inter-chain disulfide bonds of Abs, more particularly monoclonal Abs (mAbs). Antibodies of different antibody classes contain different numbers of inter-chain disulfide bonds. For example, IgG1 antibodies typically have four inter-chain disulfide bonds, all four located in the hinge region, and after (partial) reduction of the disulfide bonds the linker-drug is randomly attached to free thiol groups.

Compounds of formula (I) and (II) for use in accordance with the present invention can be obtained according to methods and procedures that are well known to a person skilled in the art. Conjugation through inter-chain disulfide bonds can occur after complete or partial reduction of said disulfide bonds. Suitable methods for preparing such compounds can be found in the description and examples of Applicant's WO2011/133039A. In particular, Example 15 of WO2011/133039A describes the partial reduction of trastuzumab to generate 2 free thiol groups per mAb and conjugation with a number of linker-drugs to ADCs having an average DAR of approx. 2. It is easily understood by those skilled in the art how to obtain ADCs having an average DAR of from 1 to 4. Examples 7 and 8 of WO2005/084390A describe partial reduction, partial reduction/partial re-oxidation, and complete reduction strategies for (partial) loading of antibodies (with the linker-drug vcMMAE).

IHC and FISH status of the tumour tissue are determined using known tests, procedures, and equipment. In accordance with the present invention HER2 gene amplication can be measured using either fluorescence (FISH), chromogenic (CISH) or any other in situ hybridization test. Suitable tests for determination of the HER2 membrane expression status of the tumour tissue like the HercepTest™ (Dako Denmark) are commercially available. Further HER2 IHC tests are marketed by Ventana Medical Systems (PATHWAY anti-HER2/neu), Biogenex Laboratories (InSite™ HER2/neu), and Leica Biosystems (Bond Oracle™ HER2 IHC). HER2 FISH/CISH tests can be obtained from Abbott Molecular (PathVysion HER2 DNA Probe Kit), Life Technologies (SPOT-Light® HER2 CISH Kit), Dako Denmark (HER2 CISH PharmDx™ Kit), Dako Denmark (HER2 FISH PharmDx™ Kit), and Ventana Medical Systems (INFORM HER2 Dual ISH DNA Probe Cocktail).

The present invention also relates to the use of a compound of formula (I) or (II) for the treatment of patients (i.e. women) having endometrial cancer, in particular USC, which is HER2 IHC 2+ or 1+ and/or HER2 FISH negative as described herein above.

The present invention further relates to the use of a combination of a compound of formula (I) or (II) with a therapeutic antibody and/or a chemotherapeutic agent, for the treatment of endometrial cancer, in particular for the treatment of USC.

In one embodiment of the present invention, the therapeutic antibody for use in combination with a compound of formula (I) or (II) in accordance with the present invention is pertuzumab, bevacizumab or trastuzumab, and the chemotherapeutic agent is i) a taxane, particularly docetaxel or paclitaxel, ii) a DNA damaging agent, particularly cisplatin, carboplatin or oxaliplatin, iii) a topoisomerase inhibitor, particularly topotecan or irinotecan, iv) an anthracycline, particularly doxorubicin, liposomal doxorubicin, epirubicin, daunorubicin or valrubicin, more particularly doxorubicin, v) an mTOR inhibitor, particularly temsirolimus, or vi) a tyrosine kinase inhibitor, particularly lapatinib or afatinib.

In another embodiment of the present invention, the therapeutic antibody for use in combination with a compound of formula (I) or (II) in accordance with the present invention is pertuzumab and the chemotherapeutic agent is a taxane, particularly docetaxel or paclitaxel, an anthracycline, particularly doxorubicin, epirubicin, daunorubicin or valrubicin, more particularly doxorubicin, or a tyrosine kinase inhibitor, particularly afatinib.

The present invention further relates to the use of a combination of a compound of formula (I) or (II) with another ADC, such as for example T-DM1, for the treatment of human solid tumours and haematological malignancies expressing HER2, in particular human solid tumours expressing HER2.

The present invention further relates to a pharmaceutical composition comprising a compound of formula (I) or (II) or a combination with a therapeutic antibody and/or a chemotherapeutic agent thereof as described herein above, and one or more pharmaceutically acceptable excipients.

Typical pharmaceutical formulations of therapeutic proteins such as monoclonal antibodies and (monoclonal) antibody-drug conjugates take the form of lyophilized powders or cakes, which require (aqueous) dissolution (i.e. reconstitution) before intravenous infusion, or frozen (aqueous) solutions, which require thawing before use. Particularly, in accordance with the present invention the pharmaceutical composition is provided in the form of a lyophilized cake.

Suitable pharmaceutically acceptable excipients for inclusion into the pharmaceutical composition (before freeze-drying) in accordance with the present invention include buffer solutions (e.g. citrate, histidine or succinate containing salts in water), lyo protectants (e.g. sucrose, trehalose), tonicity modifiers (e.g. sodium chloride), surfactants (e.g. polysorbate), and bulking agents (e.g. mannitol, glycine). Excipients used for freeze-dried protein formulations are selected for their ability to prevent protein denaturation during the freeze-drying process as well as during storage.

The sterile, lyophilized powder multi-dose formulation of Herceptin™ contains 440 mg trastuzumab, 400 mg α,α-trehalose dihydrate, 9.9 mg L-histidine. HCl, 6.4 mg L-histidine, and 1.8 mg polysorbate 20, USP. Reconstitution with 20 ml of Bacteriostatic or Sterile Water for Injection (BWFI or SWFI) yields a multi-dose solution containing 21 mg/ml trastuzumab at a pH of approximately 6. The sterile, lyophilized powder single-use formulation of Kadcyla™ contains upon reconstitution 20 mg/ml ado-trastuzumab emtansine, 0.02% w/v polysorbate 20, 10 mM sodium succinate, and 6% w/v sucrose with a pH of 5.0.

A therapeutically effective amount of the compound of formula (I) or (II) for use in accordance with the present invention lies in the range of about 0.01 to about 15 mg/kg body weight, particularly in the range of about 0.1 to about 10 mg/kg, more particularly in the range of about 0.3 to about 10 mg/kg body weight. This latter range corresponds roughly to a flat dose in the range of 20 to 800 mg of the ADC compound. The compound for use in accordance with the present invention is administered weekly, bi-weekly, three-weekly or monthly, for example weekly for the first 12 weeks and then every three weeks until disease progression. Alternative treatment regimens may be used depending upon the severity of the disease, the age of the patient, the compound being administered, and such other factors as would be considered by the treating physician.

EXAMPLES

In Vitro USC Cell Line Cytotoxicity

Nine primary USC cell lines were evaluated for HER2 surface expression by IHC and flow cytometry (FACS) and for HER2 gene amplification by FISH as described by D. P. English et al. in Cancer Medicine published by John Wiley & Sons Ltd., pp. 1-10, 2014.

SYD985 was 50 to 160 times more potent when compared to T-DM1 in primary USC cell lines with HER2 IHC 1+ and IHC 2+ expression. In a set of three HER2 IHC 1+USC cell lines the average $IC_{50}$s for SYD985 and T-DM1 were 0.07 µg/ml and 3.58 µg/ml, respectively (p=0.004); in a set of three HER2 IHC 2+USC cell lines the average $IC_{50}$s were 0.02 µg/ml and 1.82 µg/ml, respectively (p=0.005); and in a set of three HER2 NC 3+USC cell lines the average $IC_{50}$s were 0.01 µg/ml and 0.04 µg/ml, respectively (p=0.06).

FIG. 1 shows representative in vitro dose-response curves of SYD985 versus T-DM1 for HER2 IHC 3+, 2+, and 1+USC cell lines.

In Vivo USC Cell Line Xenograft Efficacy in Mice

Five- to 8-week old female SCID mice (Harlan, Netherlands) were given a single intra-peritoneal (i.p.) injection of $7.5 \times 10^6$ USC ARK-2 cells (i.e. HER2 IHC 3+, FISH positive) in approx. 400 µl phosphate-buffered saline solution. After a 7-day period to allow for tumour establishment, two groups of 5 mice were treated with either SYD985 (5 mg/kg/wk i.v.) or T-DM1 (5 mg/kg/wk i.v.). No signs of general toxicity were seen in any of the treatment groups. The mice in all treatment groups were given series of five injections after which they were placed in follow-up and observed for overall survival as the primary outcome.

Figure 2:
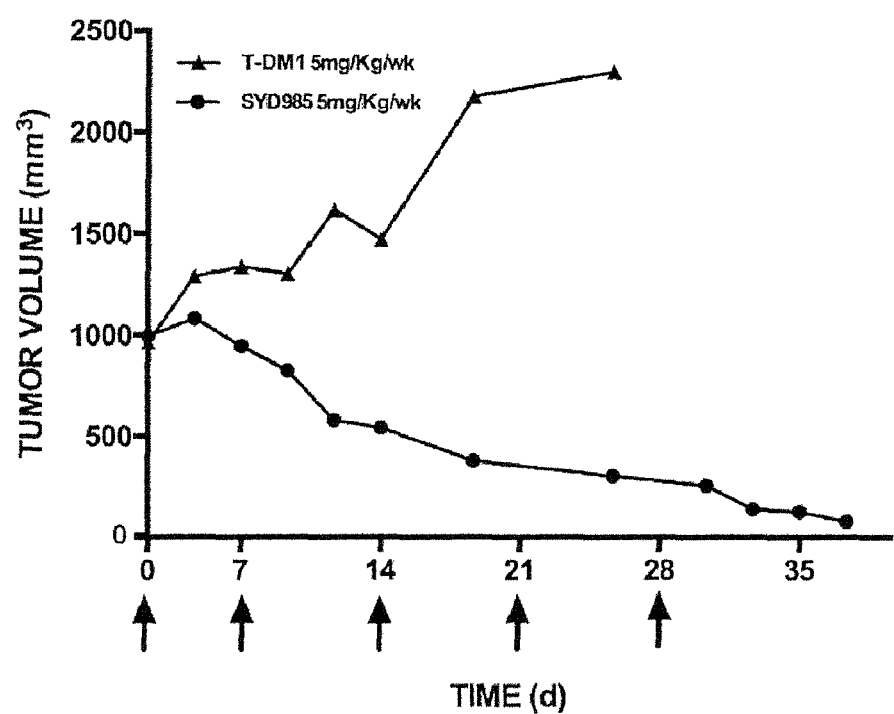
FIG. 2. In vivo USC cell line xenograft efficacy in mice: SYD985 versus T-DM1 after multiple injections.

FIG. 2 shows the in vivo USC cell line xenograft efficacy in mice of SYD985 versus T-DM1 after multiple injections.

In Vivo USC Cell Line Xenograft Efficacy Study in Mice

USC ARK-2 cells (i.e. HER2 IHC 3+, FISH positive) were expanded in culture, washed and injected (with Matrigel™) at a concentration of 7 million cells subcutaneously into 5-8 weeks old SCID mice. Once the tumors reached approx. 200 mm³ in volume they were randomly divided in 5 groups keeping average tumor volume similar between groups. There were a total of 8-10 animals in each group.

The animals were treated with a single, intra-venous injection of vehicle, T-DM1 at 10 mg/kg or SYD985 at 10 mg/kg. Tumor size and weight of the animals were recorded for 21 days. Survival data were recorded for 30 days.

Figure 3:
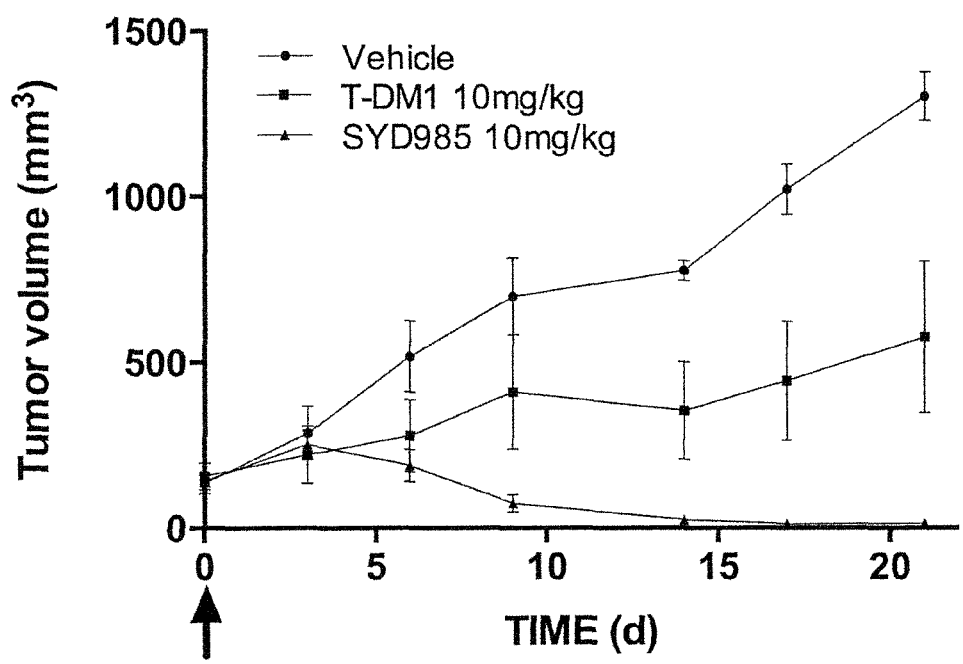
FIG. 3. In vivo USC cell line xenograft efficacy in mice: SYD985 versus T-DM1 after single injection at day 0.

FIG. 3 shows the in vivo USC cell line xenograft efficacy in mice of SYD985 versus T-DM1 after single injection at day 0.

The invention claimed is:

1. A method of treating uterine serous carcinoma expressing HER2 in a human patient, comprising administering to the patient a therapeutically effective amount of a compound having the structure

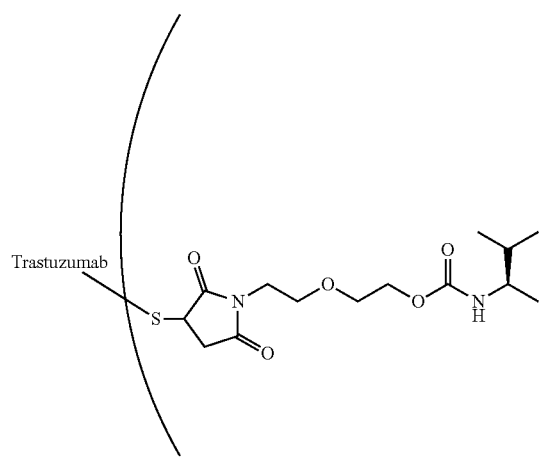
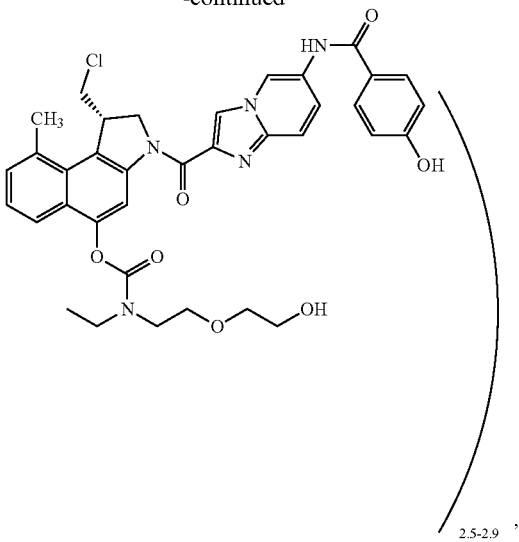

wherein 2.5-2.9 represents an average DAR for the compound.

2. The method of claim 1, further comprising administering an effective amount of a therapeutic antibody or a chemotherapeutic agent, or a combination thereof.

3. The method of claim 2, wherein the therapeutic antibody is pertuzumab and the chemotherapeutic agent is a taxane, an anthracycline or a tyrosine kinase inhibitor.

4. The method of claim 3, wherein the taxane is docetaxel or paclitaxel, the anthracycline is doxorubicin, epirubicin, daunorubicin, or valrubicin, and the tyrosine kinase inhibitor is afatinib.

5. The method of claim 1, wherein the average DAR for the compound is from 2.6 to 2.9.

6. The method of claim 5, wherein the compound is administered in an amount of from about 0.3 mg/kg to about 10 mg/kg.

7. The method of claim 6, wherein the compound is administered every three weeks.

8. The method of claim 1, wherein the patient is administered a pharmaceutical composition, comprising the compound as defined in claim 1 and one or more pharmaceutically acceptable excipients.

9. The method of claim 8, wherein the pharmaceutical composition is suitable for intravenous infusion.

10. The method of claim 8, wherein the pharmaceutical composition is in the form of a lyophilized powder or a frozen solution.

11. The method of claim 1, wherein the uterine serous carcinoma is HER2 IHC 3+.

* * * * *